United States Patent

Hogg

[11] 3,939,409
[45] Feb. 17, 1976

[54] PARTICLE STUDY DEVICE AND SAMPLE METERING MEANS USED THEREIN

[75] Inventor: Walter R. Hogg, Miami Lake, Fla.

[73] Assignee: Coulter Electronics, Inc., Hialeah, Fla.

[22] Filed: Aug. 1, 1974

[21] Appl. No.: 493,828

[52] U.S. Cl.......... 324/71 CP; 73/422 TC; 222/217
[51] Int. Cl.².................. G01N 27/07; G01F 13/00
[58] Field of Search....... 324/30 B, 71 CP; 222/207, 222/217, 216, 344; 73/422 TC

[56] References Cited
UNITED STATES PATENTS

| 80,847 | 8/1868 | Wheeler | 222/217 |
|---|---|---|---|
| 2,877,929 | 3/1959 | Ireland | 222/388 |
| 3,087,438 | 4/1963 | Ciesielski | 417/207 |
| 3,115,280 | 12/1963 | Battista | 222/386.5 |
| 3,653,266 | 4/1972 | Holmes | 222/367 |
| 3,688,191 | 8/1972 | Claps | 324/71 CP |
| 3,714,565 | 1/1973 | Coulter et al. | 324/71 CP |
| 3,859,012 | 1/1975 | Hogg | 417/437 |

Primary Examiner—Alfred E. Smith
Assistant Examiner—Wm. H. Punter
Attorney, Agent, or Firm—Silverman & Cass, Ltd.

[57] ABSTRACT

A particle study device includes a sample metering device having an input for receiving a sample of particulate matter, a drain for expelling the sample of particulate matter, an ejection port, and means for trapping a volume of sample within the device. The sample metering device also includes an ejecting device operative to eject a predetermined amount of the trapped sample through the ejecting port. A coupling device coupled to the sample metering device, a source of diluent and the sensing zone in the particle study device, combines the ejected predetermined amount of particulate matter and diluent to form a liquid suspension and couples the liquid suspension to the sensing zone.

34 Claims, 3 Drawing Figures

U.S. Patent Feb. 17, 1976 3,939,409
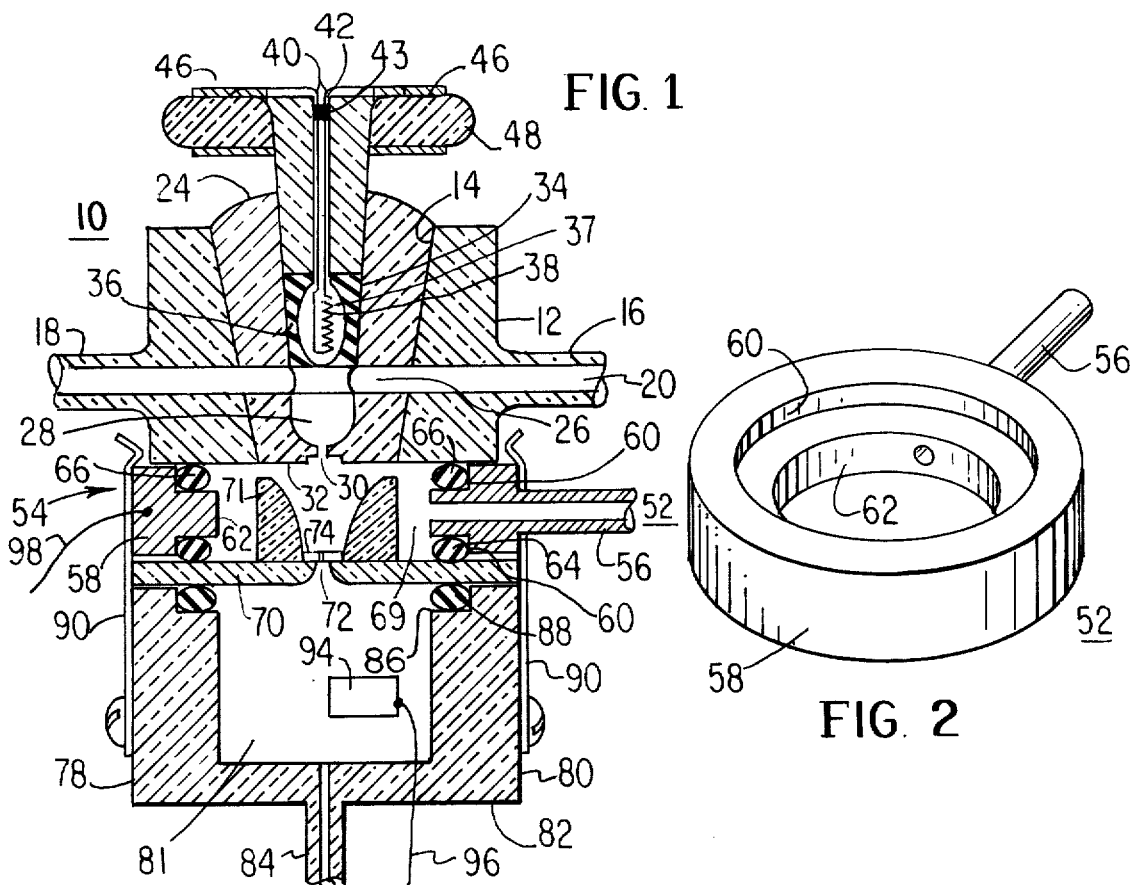
FIG. 1
FIG. 2
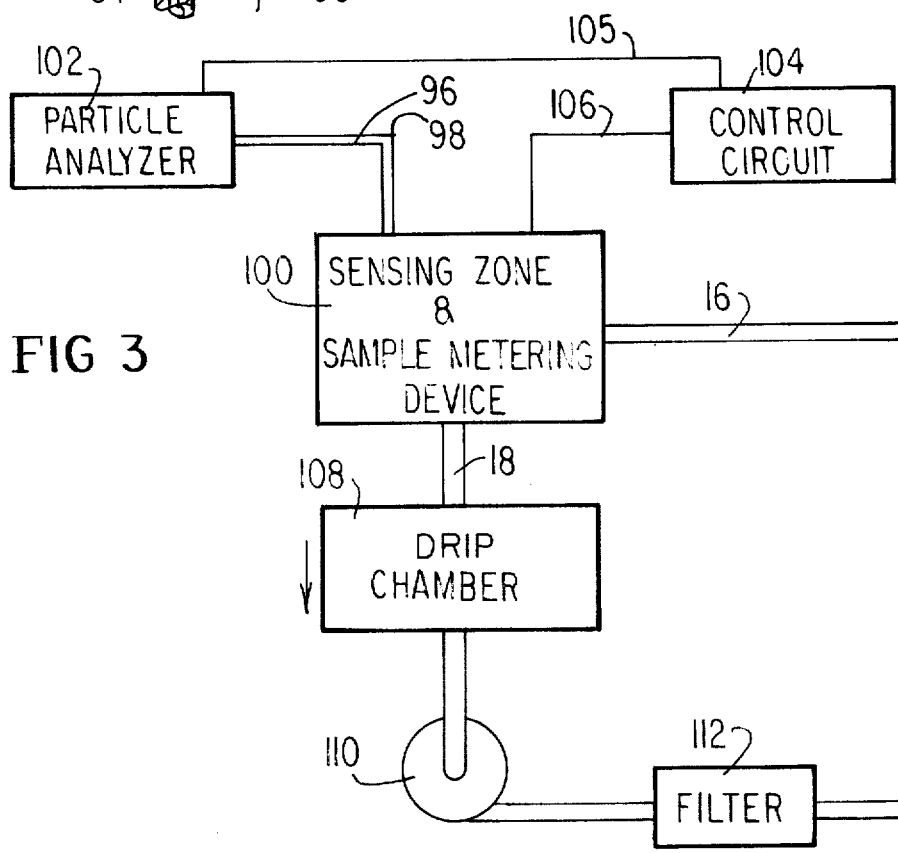
FIG 3

PARTICLE STUDY DEVICE AND SAMPLE METERING MEANS USED THEREIN

CROSS REFERENCE TO RELATED APPLICATIONS

This application is related to U.S. patent application Ser. No. 279,436 filed Aug. 10, 1972, now U.S. Pat. No. 3,859,012, issued Jan. 7, 1975, which is, to the extent necessary, to be considered incorporated herein by this reference.

BACKGROUND OF THE INVENTION

This invention relates to particle study devices and more specifically to a device for ejecting a specific amount of particulate matter into a diluent stream leading to a sensing zone.

In the field of particle analysis and study, particles to be counted and sized are passed through a sensing zone in a particle study device such as a Coulter type particle study device which operates on the Coulter sensing principle disclosed in U.S. Pat. No. 2,656,508, issued Oct. 20, 1953 to Wallace H. Coulter.

In a Coulter type particle study device an electrode extends into an electrolyte on each side of an insulating wall. The insulating wall has a minute aperture formed therein, commonly referred to as a Coulter aperture. An electrical excitation is applied causing electric current to flow between the electrodes through the Coulter aperture. According to the Coulter principle, particles passing through the aperture from one body of electrolyte to the other body of electrolyte will change the impedance of the electrolyte contained within the aperture. This change in impedance coacting with the electrical excitation causes a particle pulse to be developed. The particle pulse is coupled to a particle analyzer in the particle study device in order to provide a particle count and in order to provide an indication of the particle size or volume.

Heretofore, it has been common practice to employ the fluid electrolyte for diluting a sample of particles to be studied. The dilution is necessary because the particles to be studied most often exist in a very high concentration. The amount of particles in a small sample is most often so great that a small quantity, passing through the sensing zone, would pass through so quickly that they could not be accurately counted and sized. Furthermore, it is generally only necessary to study or analyze a very small amount of particulate matter in order to be able to ascertain the number in a specific volume and the size of the particulate matter. For example, blood generally has approximately 5,000,000 cells per cubic millimeter, and it is only necessary to study or analyze one hundredth of that amount, namely, a volume of 0.01 cubic millimeters.

The dilution of particulate matter to be studied has most commonly been performed by trained technicians. This process of diluting a specific amount of particulate matter in a specific volume of diluent was time consuming and had to be performed in an extremely careful fashion in order to provide an accurate count. This time consuming, tedious task prevented the trained technician from engaging in other, more profitable activities.

Recently, an ejecting mechanism has been developed, such as is described in the above mentioned incorporated by reference patent application, which ejects a predetermined amount of particulate matter into an electrolyte diluent leading to the sensing zone in the particle study device. This ejecting mechanism, although eliminating the necessity for precisely diluting a sample of particulate matter to be studied, has the disadvantage that it must first be manually loaded with a sample of particulate matter via an input port, then inserted into the particle study device and operated for ejecting a portion of the particles. After operation, the ejecting mechanism must again be removed, cleaned of remaining sample and manually refilled. This procedure, although it eliminates the precise dilution process previously required, is still unnecessarily time consuming and tedious.

SUMMARY OF THE INVENTION

In practicing this invention a particle study device is provided wherein particulate matter in fluid suspension is passed through a sensing zone for counting and sizing the particulate matter. The particle study device includes a sample metering mechanism having an input for receiving a sample of particulate matter, a drain for expelling the sample of particulate matter, an ejection port and means for trapping a volume of sample within the metering mechanism. The sample metering mechanism also includes an ejecting mechanism operative to eject a predetermined amount of the trapped sample through the ejecting port. A coupling structure, coupled to the sample metering mechanism to a source of electrolyte diluent and a sensing zone allows combination of the ejected predetermined amount of particulate matter and diluent to form the liquid suspension. The coupling mechanism also couples the fluid suspension to the sensing zone.

In one embodiment a sample metering mechanism in the particle study device includes a stopcock assembly. The stopcock assembly has a stopcock valve rotatably mounted therein. The valve has a sample accumulation chamber formed in it, an input port, a drain port and an ejection port are also formed in the valve and are in communication with the sample accumulation chamber. The input and drains previously noted are formed in the assembly. The stopcock valve is rotatable to a first position for aligning the input and input port and the drain and drain port for receiving and expelling a sample of particulate matter. The stopcock valve is also rotatable to a second position for blocking the input and the drain ports and trapping a volume of sample in the accumulation chamber.

In all embodiments, the ejecting mechanism includes a thermal expansion device such as is shown and described in the patent application which is incorporated by reference herein.

BRIEF DESCRIPTION OF THE DRAWINGS

FIG. 1 is a section view of the sample metering device and sensing zone structure of this invention;

FIG. 2 is a perspective view of the electrolyte flow assembly shown in FIG. 1;

FIG. 3 is a block diagram of the improved particle study device of this invention showing the sample metering device and structure of the sensing zone as a block within the block diagram.

DESCRIPTION OF THE PREFERRED EMBODIMENT

Referring to FIG. 1, the specific embodiment of the sample metering structure shown is a stopcock assembly 10 and includes a housing 12 formed from glass or other insulating material. The housing includes a truncated cone shaped chamber 14. Pipes 16 and 18 are formed onto housing 12 and include a conduit 20 passing therethrough and connecting with chamber 14. These pipes constitute input and output ports respectively.

A stopcock valve 24 is fitted into chamber 14 and rotates therein. Stopcock valve 24 has a conduit 26 passing therethrough which connects with conduit 20 in pipes 16 and 18 when stopcock valve 24 is rotated to a first position. Conduit 26 connects with a sample accumulation chamber 28 formed substantially in the center of stopcock valve 24. A minute opening 30 is formed in sidewall 32 of stopcock valve 24 and connects with chamber 28 thereby providing three separate openings to chamber 28 in stopcock valve 24.

Positioned in chamber 28 of stopcock valve 24 is an expansive element 34 such as is shown and described in U.S. Patent application Ser. No. 279,436 which is incorporated by reference. Expansive element 34 includes an elastic outer member 36 surrounding a thermal expansion element 37. A resistor 38 is embedded in the thermal expansion element 37. Wires 40 secured to the terminals of resistor 38 pass through thermal expansion element 37 and elastic outer member 36 and extend through an aperture 42 formed in handle 44 of stopcock valve 24. Handle 44 is inserted into end of chamber 28 after insertion of the expansive element 34 in order to seal the chamber from the external environment. After expansive element 34 is inserted, the aperture 42 is filled with a sealant 43. Wires 40 then are connected to contact terminals 46 on portion 48 of handle 44 in order to provide a convenient means of connecting expansive element 34 with the equipment with which it is associated.

The stopcock assembly 10 is positioned adjacent and bears against a coupling means which, in the embodiment shown, takes the form of a ring-shaped electrolyte flow assembly 52, which is shown in perspective in FIG. 2. In the preferred embodiment, electrolyte flow assembly 52 can be formed primarily from stainless steel or some other equally effective noncorrosive conductive member so as to eliminate the need for a separate electrode in this portion of the particle study device. However it can be formed from an insulating material such as glass with a separate electrode provided. The electrolyte flow assembly 52 includes a ring shaped housing member 54 which is formed from one of the conductive or insulating material as noted. A tube 56 is formed in the sidewall 58 of ring shaped housing member 54 and extends radially therefrom. Annular groves 60 are formed at the corners of the inner surface 62 of housing member 54 and rings 64 and 66 are seated in these annular groves 60.

The electrolyte flow assembly 52 is seated on a wall or plate 70 formed from glass or other insulating material and forms a chamber 69 above plate 70. A minute aperture 72 is formed in the center of plate 70 and a ruby or sapphire wafer 74 having a microscopic aperture therethrough is secured to plate 70 surrounding aperture 72 in order to form what is commonly known in the art as a Coulter aperture. An annular ring 71 is formed of glass, is positioned on and secured to the top surface of plate 70.

Plate 70 is seated on a cylindrically shaped housing 78, formed of glass or other insulating material and having cylindrical sidewalls 80 and a bottom wall 82. Housing 78 defines a suspension accumulation chamber. A conduit tube 84 is formed in the center of bottom wall 82 and extends downwardly perpendicular to the plane of bottom wall 82. The top edges of sidewall 80 have an annular groove 86 formed therein and an O-ring 88 is seated in annular groove 86 in order to provide a seal between housing 78 and plate 70.

The entire assembly consisting of electrolyte flow assembly 52, plate 70 and cylindrical shaped housing 78 is held together via clamps 90. A second electrode 94 is positioned in the chamber 81 formed by sidewall 80 and bottom wall 82 of cylindrical shaped housing 78. A conductor 96 connects electrode 94 to the external particle analyzing apparatus in the same manner as conductor 98, secured to sidewall 58 of ring-shaped housing 54 is connected to the particle analyzing apparatus.

In operation, handle 44 of stopcock valve 24 is turned to a first position, either manually or via an automatic control mechanism such as a pneumatic control mechanism. In the first position, conduit 20 is connected directly to conduit 26 and chamber 28 allowing a sample of blood or some other particulate laden matter to be analyzed to be entered into chamber 28. The sample of blood or other particulate matter may be forced into chamber 28 via suction drawing on conduit 20, or via pressure forcing the fluid into conduit 20 and chamber 28. When the sample has been entered into chamber 28, handle 44 is moved to its second position, turning stopcock valve 24 and breaking the connection between conduit 26 and conduit 20. The entire stopcock assembly 10, if not presently in position, may be placed on electrolyte flow assembly 52 such as is shown in FIG. 1 with O-ring 66 forming the seal so as to prevent the escape of any electrolyte or sample diluted in the electrolyte.

If the chamber 28 in stopcock assembly 10 is filled while in position on electrolyte flow assembly 52, all fluid connections to chambers 69 and 81 therein including connections not shown such as, for example, connections to provide fluid to flush the chambers, must be closed off by appropriate valves creating a pressure differential to prevent flow through aperture 30 into chamber 28. This forces chamber 28 to be filled only with the sample of blood via conduit 20. If the chamber 28 is not in position on electrolyte flow assembly 52 when it is filled opening 30 can be plugged with an appropriate device to prevent entry of air into chamber 28 via opening 30. Alternatively, if the sample is forced into chamber 28 slowly the low pressure will not create sufficient suction to draw air into chamber 28 through opening 30, since surface tension provides a fairly effective barrier against flow through a microscopic passageway which is wet on one side only.

Electrolyte is allowed to enter the electrolyte flow assembly 52 via tube 56 and fill the center area or coupling chamber of electrolyte flow assembly 52. Trapped air may be avoided by filling chambers 69 and 81 before affixing stopcock valve 24 or by other means known in the art. The electrolyte is forced to flow around annular ring 71 causing the fluid to flow past opening 30. The electrolyte will pass through aperture 72 in plate 70 filling the cavity formed by cylindrical shaped housing 78 and providing a conductive current path between the electrode formed from ring-shaped housing member 54 and conductor 98 and electrode 94 and conductor 96.

The electrodes 46 in portion 48 of handle 44 are connected to the control mechanism previously noted which will be explained in greater detail in a subsequent portion of this application. The control mechanism generates a control signal which may be a voltage, or current, that is coupled to the electrodes 46 and, via conductors 40 to resistor 38 in expansive element 34. The heat generated by resistor 38 will cause thermal expansion element 37 to expand and force a minute, precise quantity of sample from chamber 28 through aperture 30. This minute, precise amount of sample will proceed directly to the aperture surrounded by the electrolyte flow assembly 52. The sample particles in electrolyte solution in electrolyte flow assembly 52 will pass through the aperture in wafer 74 causing a change in impedance between electrode 94 and the electrode formed by housing member 54 of electrolyte flow assembly 52. This change in impedance will be sensed by the particle analyzing device for counting the particles and analyzing various characteristics of the particles.

Referring now to FIG. 3, the entire apparatus shown in FIG. 1, consisting of stopcock assembly 10, ring shaped flow assembly 52, aperture plate 70, and cylindrically shaped housing 78 is shown generally as 100 and will hereinafter be referred to as sensing zone and sample metering device 100. A particle analyzer 102 of the Coulter type, such as shown and described in U.S. Pat. No. 2,656,508, is coupled to sensing zone and sample metering device 100 via conductors 96 and 98. The terminations of conductors 96 and 98 are shown in greater detail in FIG. 1. Particle analyzer 102 supplies electrical excitation to electrodes 94 and the electrode formed by housing member 54 in FIG. 1 via conductors 96 and 98. The passage of particles through the sensing zone in sensing zone and sample metering device 100 will cause a modulation of the electrical excitation which will be detected by particle analyzer 102 and can be used for counting and sizing the particles.

A control circuit 104 is shown as being coupled to sensing zone and sample metering device 100. Control conduit 104 includes circuitry for developing a control signal which is coupled via conductor 106 to terminals 46 on handle portion 48 of stopcock valve 24. This control signal will cause resistor 38 in expansive element 34 to heat up and cause an expansion of the thermal expansion element 37. Control circuit 104 may also include a solenoid mechanism and logic circuit. The solenoid mechanism will be coupled to handle portion 48 of stopcock valve 24 and is operative to rotate handle portion 48 so as to move stopcock valve 24 to its first or second position. The logic circuit in control circuit 104 is operative when stopcock valve 24 has been moved to its second position to develop the control signal which is coupled to expansive element 34. Control circuit 104 may be programmed to switch from the first to second position at certain intervals or may be manually actuated. The control signal may also be coupled to particle analyzer 102 via conductor 105 for initiating operation thereof when the sample is ejected. Particle analyzer 102 can include a pulse rate meter which develops a rate signal in response to a reduction in the pulse rate, thus indicating the ejection and counting of substantially all particles in the sample. The rate signal can stop operation of analyzer 102 and can be coupled to additional logic circuitry in control circuit 104 via conductor 105 or another appropriate conductor. Control circuit 104 will operate in response to the rate signal to either terminate the control signal or initiate another operation cycle immediately or after a timed interval.

Pipe 84 shown in FIG. 1, couples sensing zone and sample metering device 100 to a drip chamber 108. Drip chamber 108 is of the type shown and described in U.S. Pat. Nos. 3,340,470 and 3,340,471, assigned to the same assignee as this application. The output of drip chamber 108 is coupled to the input of a pump 110 and the output of pump 110 is coupled to a filter 112. The output of filter 112 is coupled to pipe 16.

In operation, the particle laden diluent electrolyte, which has passed through the sensing zone and sample metering device 100, passes via pipe 18 to drip chamber 108. Drip chamber 108 breaks any electrical connection caused by the electrolyte diluent thus preventing the short-circuiting of signals away from the input of the particle analyzer 102. The electrolyte diluent passing through drip chamber 108 is pumped by pump 110 to filter 112 which removes the particulate matter. The output of filter 112 is, therefore, filtered diluent electrolyte which is pumped to pipette 16 and is reused in the operation of the sample metering device.

Although the particle study device has been shown and described with a stopcock assembly, it is to be understood that other device implementations are also envisioned as being within the scope of this application. For example, rather than a stopcock assembly, a tube with chamber therein may be substituted. On each side of the chamber could be situated two pneumatically controlled valves having a first and second position for allowing passage of the particulate laden matter through the tube and chamber or for sealing the tube and chamber so as to trap a predetermined quantity of particulate matter within the chamber. The chamber will include an expansive element similar to expansive element 34 and an aperture similar to aperture 30 such that the entire above described apparatus can be secured to electrolyte flow assembly 52 in place of the stopcock assembly as shown in FIG. 1.

Additionally, the stopcock assembly 10 shown in FIG. 1 can be constructed so as to be initially positioned between a hypodermic needle and syringe such that when a blood sample is drawn, it will be drawn through pipe 16, chamber 28 and pipe 18 into the syringe. The entrance of air through aperture 30 is prevented by means of a soft rubber cap, covering aperture 30 held in place by suitable clamps. When the full blood sample is drawn, the chamber 28 would be filled and the stopcock valve 24 would be turned to its second position sealing the blood sample in the chamber. The hypodermic needle, syringe and stopcock assembly can be disassembled, the needle discarded, the blood sample in the syringe sent to a laboratory for full analysis, and the stopcock assembly 10 sent to the laboratory where it is attached to the mechanism as shown in FIGS. 1, 2 and 3 for immediate analysis of a small portion of the blood sample. Upon completion of the testing, the entire stopcock assembly 10 can be sterilized and reused. Use of the assembly in this fashion will, of course, eliminate the need for complex, separate dilution of blood samples, or other particulate matter samples prior to usage in a particle study device of the Coulter type.

What it is desired to secure by Letters Patent of the United States is:

1. In a particle study device wherein particulate matter in liquid suspension is passed through a sensing zone the improvement comprising a sample metering means having an input for receiving a sample of particulate matter, a drain for expelling a sample of particulate matter, an ejection port, and means for trapping a volume of sample therein, said sample metering means further including an ejecting means operative to eject a predetermined amount of said trapped volume of sample through said ejecting port, and coupling means coupled to said sample metering means to, a source of diluent and to said sensing zone for combining said ejected predetermined amount of said trapped sample and diluent to form said liquid suspension and for coupling said liquid suspension to said sensing zone.

2. The device of claim 1 wherein said ejecting means includes thermal expansion means operative in response to a control signal to expand and eject said predetermined amount of said trapped sample.

3. The device of claim 2 wherein said thermal expansion device includes an electric heating element, an expandable element surrounding said heating element and having a given thermal-coefficient of expansion, and an insulating jacket surrounding said expandable element and said heating element and expandable therewith.

4. The device of claim 1 wherein said means for trapping a volume of sample therein includes a sample accumulation chamber formed in said sample metering means.

5. The device of claim 4 wherein said means for trapping a volume of sample therein, further includes shutoff means coupling said sample accumulation chamber to said input and to said drain, said shutoff means being operative in a first position to allow sample to pass through said accumulation chamber from input to drain and operative in a second position to trap said volume of sample within said chamber.

6. The device of claim 5 wherein said ejecting means is operative to eject said predetermined amount of said trapped sample when said shutoff means is in said second position.

7. The device of claim 5 wherein said ejecting means includes thermal-expansion means operative when said shutoff means is in said second position to expand and eject said predetermined amount of said trapped sample.

8. The device of claim 5 wherein said shutoff means includes a first shutoff valve coupling said sample accumulation chamber to said input and a second shutoff valve coupling said sample accumulation chamber to said drain.

9. The device of claim 8 wherein said first and second shutoff valves are electrically operated shutoff valves.

10. The device of claim 8 wherein said first and second shutoff valves are manually operated shutoff valves.

11. The device of claim 1 wherein said sample metering means includes a stopcock assembly having a stopcock valve rotatably mounted therein, said stopcock assembly forming said means for trapping a volume of sample therein, said stopcock valve having a sample accumulation chamber formed therein and an input port, drain port and ejection port formed therein and in communication with said sample accumulation chamber, said input port being said sample input, said output port being said output, said assembly having said input and drain formed therein, said stopcock valve being rotatable to a first position for aligning said input and input port and drain and drain port for receiving and expelling said sample, said stopcock valve being rotatable to a second position for blocking said input and drain port and trapping said volume of sample in said accumulation chamber.

12. The device of claim 11 wherein said ejecting means is positioned in said sample accumulation chamber.

13. The device of claim 11 wherein said ejecting means includes thermal-expansion means positioned in said sample accumulation chamber.

14. The device of claim 1 wherein said coupling means includes, a housing defining a coupling chamber and a conduit coupled to said coupling chamber and said source of diluent for coupling said diluent to said coupling chamber, said coupling chamber being in communication with said ejecting port and said sensing zone for combining said ejected predetermined amount of said trapped sample and diluent to form said liquid suspension and for coupling same to said sensing zone.

15. The device of claim 14 wherein said housing is formed from an electrically conductive material.

16. The device of claim 1 wherein said sensing zone includes a wall in communication with said coupling means and an aperture formed in said wall for allowing said liquid suspension therethrough, said device further including a suspension accumulation chamber coupled to said wall for receiving said liquid suspension passing through said aperture, a first electrode positioned on one side of said wall and a second electrode positioned on the other side of said wall in said suspension chamber.

17. The device of claim 16 wherein said coupling means forms said first electrode.

18. A sample metering device for use in a particle study device wherein particulate matter is passed through a sensing zone including in combination, an input for receiving a sample of particulate matter, a drain for expelling the sample of particulate matter, an ejection port and means for trapping a volume of sample therein, said device further including an ejecting means operative to eject a predetermined amount of said trapped sample through said ejecting port.

19. The sample metering device of claim 18 wherein said ejecting means includes thermal-expansion means operative in response to a control signal to expand and eject said predetermined amount of said trapped sample.

20. The sample metering device of claim 19 wherein said thermal-expansion device includes an electric heating element, an expandable element surrounding said heating element and having a given thermal-coefficient of expansion, and an insulating jacket surrounding said expandable element and said electric heating element and expandable therewith.

21. The sample metering device of claim 18 wherein said means for trapping a volume of sample therein includes a sample accumulation chamber formed in said sample metering device.

22. The sample metering device of claim 21 further including shutoff means coupling said sample accumulation chamber to said input and to said drain, said shutoff means being operative in a first position to allow sample to pass through said accumulation chamber from input to drain and operative in a second position to trap said volume of sample within said chamber.

23. The sample metering device of claim 22 wherein said ejecting means is operative to eject said predetermined amount of said trapped sample when said shutoff means is in said second position.

24. The sample metering device of claim 22 wherein said ejecting means includes thermal-expansion means operative when said shutoff means is in said second position to expand and eject said predetermined amount of said trapped sample.

25. The sample metering device of claim 22 wherein said shutoff means includes, a first shutoff valve coupling said sample accumulation chamber to said input and a second shutoff valve coupling said sample accumulation chamber to said drain.

26. The sample metering device of claim 25 wherein said first and second shutoff valves are electrically operated shutoff valves.

27. The sample metering device of claim 25 wherein said first and second shutoff valves are manually operated shutoff valves.

28. The sample metering device of claim 22 wherein said shutoff means and accumulation chamber are formed in a stopcock assembly.

29. In the sample metering device of claim 18, a stopcock assembly having a stopcock valve rotatably mounted therein, said stopcock assembly forming said means for trapping a volume of sample therein, said stopcock valve having a sample accumulation chamber formed therein, an input port, drain port and ejection port formed in said stopcock valve and in communication with said sample accumulation chamber, said input port being said sample input, said output port being said output, said assembly having said input and drain formed therein, said stopcock valve being rotatable to a first position for aligning said input and input port and drain and drain port for receiving and expelling said sample, said stopcock valve being rotatable to a second position for blocking said input and drain ports and trapping a volume of sample in said accumulation chamber.

30. The sample metering device of claim 29 wherein said ejecting means is positioned in said sample accumulation chamber.

31. The device of claim 29 wherein said ejecting means includes thermal-expansion means positioned in said sample accumulation chamber.

32. In a particle study device wherein particulate matter in fluid suspension is passed through a sensing zone the improvement comprising, sample metering means including an accumulation chamber having an input port, an output port and an ejection port, shutoff means coupling said input port to a source of particulate matter and said output port to a drain, said shutoff means being operative in a first position to allow particulate matter to pass through said accumulation chamber from said source to said drain and operative in a second position to trap a volume of said particulate matter within said accumulation chamber, said accumulation chamber having an ejecting means positioned therein including a thermal-expansion device operative in response to a control signal to expand and eject a predetermined amount of said trapped particulate matter.

33. The device of claim 32 further including coupling means coupled to said sample metering means, a source of diluent and said sensing zone for combining said ejected predetermined amount of said particulate matter and diluent to form said liquid suspension and for coupling same to said sensing zone.

34. The device of claim 32 further including control means coupled to said shutoff means and said thermal expansion device and operative to automatically force a volume of particulate matter into said accumulation chamber when said shutoff means is in said first position and to switch said shutoff means between said first and second positions, said control means being further operative to develop said control signal when said shutoff means is in said second position.

* * * * *